United States Patent
Delgado, III et al.

(10) Patent No.: US 7,833,268 B2
(45) Date of Patent: Nov. 16, 2010

(54) METHOD AND APPARATUS FOR IMPLANTING AN AORTIC VALVE PROSTHESIS

(76) Inventors: Reynolds M. Delgado, III, 2107 McClendon St., Houston, TX (US) 77030; Biswajit Kar, 18815 Buffalo River Way, Houston, TX (US) 77084

(*) Notice: Subject to any disclaimer, the term of this patent is extended or adjusted under 35 U.S.C. 154(b) by 821 days.

(21) Appl. No.: 11/413,376

(22) Filed: Apr. 28, 2006

(65) Prior Publication Data

US 2006/0271173 A1 Nov. 30, 2006

Related U.S. Application Data

(60) Provisional application No. 60/675,977, filed on Apr. 29, 2005.

(51) Int. Cl.
*A61F 2/24* (2006.01)
(52) U.S. Cl. ...................... 623/2.11; 128/898
(58) Field of Classification Search ................. 623/2.11; 128/898
See application file for complete search history.

(56) References Cited

U.S. PATENT DOCUMENTS

| | | | |
|---|---|---|---|
| 4,985,014 A * | 1/1991 | Orejola | 600/16 |
| 5,011,469 A * | 4/1991 | Buckberg et al. | 604/6.11 |
| 5,190,528 A * | 3/1993 | Fonger et al. | 604/171 |
| 5,433,700 A * | 7/1995 | Peters | 604/6.14 |
| 5,458,574 A * | 10/1995 | Machold et al. | 604/101.03 |
| 5,558,644 A * | 9/1996 | Boyd et al. | 604/102.02 |
| 5,584,803 A * | 12/1996 | Stevens et al. | 604/6.16 |
| 5,613,937 A * | 3/1997 | Garrison et al. | 600/201 |
| 5,718,725 A * | 2/1998 | Sterman et al. | 623/2.11 |
| 5,752,526 A * | 5/1998 | Cosgrove | 128/898 |
| 5,792,094 A * | 8/1998 | Stevens et al. | 604/4.01 |
| 5,885,238 A * | 3/1999 | Stevens et al. | 604/6.14 |
| 6,182,664 B1 * | 2/2001 | Cosgrove | 128/898 |
| 6,183,494 B1 | 2/2001 | Amor et al. | |
| 6,210,363 B1 * | 4/2001 | Esch et al. | 604/96.01 |
| 6,425,916 B1 * | 7/2002 | Garrison et al. | 623/2.11 |
| 6,497,698 B1 | 12/2002 | Fonger et al. | |
| 6,508,777 B1 * | 1/2003 | Macoviak et al. | 604/4.01 |
| 6,726,651 B1 * | 4/2004 | Robinson et al. | 604/101.01 |
| 6,730,118 B2 | 5/2004 | Spenser et al. | |
| 2003/0109924 A1 | 6/2003 | Cribier | |

* cited by examiner

*Primary Examiner*—Gary Jackson
*Assistant Examiner*—Son Dang

(57) ABSTRACT

A method and apparatus for percutaneously implanting an aortic valve prosthesis includes a pump for pumping oxygenated blood from the left atrium into the descending aorta, during a period of time in which an aortic valve prosthesis is being implanted within a diseased aortic valve. First and second catheters are associated with the pump, and a third catheter has an end which is adapted for insertion into the ascending aorta, and the third catheter has an aortic valve prosthesis associated with another end of the third catheter.

10 Claims, 4 Drawing Sheets ial patent application Ser. No. 60/675,977 filed Apr.
METHOD AND APPARATUS FOR IMPLANTING AN AORTIC VALVE PROSTHESIS

RELATED APPLICATION

This application claims the benefit and the priority of U.S. Provisional patent application Ser. No. 60/675,977 filed Apr. 29, 2005, and entitled "Method and Apparatus for Implanting an Aortic Valve Prosthesis."

BACKGROUND OF THE INVENTION

1. Field of the Invention

The invention relates to a method and apparatus for percutaneously implanting an aortic valve prosthesis.

2. Description of the Related Art

Typically, in the case of valvular heart diseases, valvular defects are repaired by a surgical valve implantation which requires thoracotomy and extracorporeal circulation, which may include placing the patient on a heart-lung machine. Such conventional surgical techniques to repair or replace valves, such as aortic valves, present problems for patients who cannot be operated on because of an associated disease or very old age, or present problems for patients who could be operated on, but only at a very high risk. For example, in the case of aortic stenosis, which is a disease of the aortic valve in the left ventricle of the heart, the only commonly available treatment is the replacement of the stenosed aortic valve by a prosthetic valve via surgery, which in the case of elderly patients presents the previously described disadvantages. In this regard, the use of the term diseased valve, or diseased aortic valve, is meant to include aortic valves in need of replacement and/or repair due to stenosis, disease, old age, or otherwise damaged valves, requiring replacement.

Recently, it has been proposed to replace, or implant, an aortic valve prostheses in the cardiac catheterization lab of a hospital, using a balloon catheter, or balloon dilatation catheter, to deliver and implant an aortic valve prosthesis within a diseased aortic valve. Thus, a more invasive chest surgery may be avoided. The aortic valve prosthesis is catheter delivered through the aorta. An example of such a technique and apparatus is described in United States Patent Application Publication No. U.S. 2003/0109924, published Jun. 12, 2003.

A major disadvantage associated with the use of such a technique is that when the new aortic valve prosthesis is being deployed within the diseased aortic valve, the patient will have a period of loss of all blood flow during the period of time that the aortic valve prosthesis is being implanted. In the case of the foregoing described technique and aortic valve prosthesis, a balloon expandable stent is included as a part of the aortic valve prosthesis. Upon the expansion of the stent by an expandable balloon associated with the catheter, the expanded balloon occludes the orifice of the aorta for a period of time while the new aortic valve prosthesis is being deployed, or implanted. The period of time may vary depending upon how easy or how difficult it is to implant the new aortic valve prosthesis. Because of this serious disadvantage, the time taken to implant such an aortic valve prosthesis must be kept to a minimum, which in turn may affect the success of the implantation of the aortic valve prosthesis securely within the diseased aortic valve, or may affect the positioning of the aortic valve prosthesis in an optimal position within the diseased aortic valve.

Accordingly, prior to the development of the present invention, there has been no method and apparatus for implanting an aortic valve prosthesis which: may be readily performed percutaneously without chest surgery and without complete loss of blood flow from the heart to the patient's body; and can be transluminally implanted in a cardiac catheterization lab setting with minimal blood loss and relatively low risk of morbidity and mortality. Therefore, the art has sought a method and apparatus for implanting an aortic valve prosthesis which may be readily performed percutaneously without chest surgery, and without complete loss of blood flow from the heart to the patient's body; may be transluminally implanted; and may be implanted in a cardiac catheterization lab setting by a cardiologist with minimal blood loss and relatively low risk of morbidity and mortality.

SUMMARY OF THE INVENTION

In accordance with the present invention, the foregoing advantages are believed to have been achieved through the present method and apparatus for implanting an aortic valve prosthesis.

One form of the method for percutaneously implanting an aortic valve prosthesis in a heart having a septum, left and right atriums, left and right ventricles, a diseased aortic valve, and descending and ascending aortas associated with the heart, may include the steps of: percutaneously delivering a portion of a first catheter into the left atrium of the heart, the first catheter being associated with a pump; percutaneously delivering a second catheter into a portion of the descending aorta, the second catheter being associated with the pump; percutaneously delivering a third catheter into the ascending aorta, the third catheter having an aortic valve prosthesis associated with the third catheter; disposing the aortic valve prosthesis within the diseased aortic valve and implanting the aortic valve prosthesis within the diseased aortic valve; and pumping oxygenated blood from the left atrium into the descending aorta, during a period of time while the aortic valve prosthesis is being implanted within the diseased aortic valve.

Another feature of this aspect of the method may include the steps of: removing the first catheter from the left atrium; removing the second catheter from the descending aorta; and removing the third catheter from the ascending aorta. Another feature is that the period of time while the oxygenated blood is being pumped may begin shortly before the aortic valve prosthesis is being implanted and may end after the aortic valve prosthesis has been implanted. An additional feature of this aspect of the invention may include the steps of pumping the oxygenated blood through the first catheter into the pump, and then pumping the oxygenated blood through the second catheter. An external pump may be utilized as the pump. An aortic valve prosthesis may be utilized which includes a stent, and the stent may be mounted on the third catheter. Another feature of this aspect of the present invention is that a self-expanding stent may be utilized as the stent, or a balloon-expandable stent may be utilized as the stent. A dilatation catheter may be utilized as the third catheter which is used to expand the stent. A further feature of the present invention may include the steps of delivering the first catheter through a femoral artery into the right atrium; and then delivering a portion of the catheter through the septum of the heart into the right atrium.

In accordance with another aspect of the present invention, an apparatus for percutaneously repairing a diseased aortic valve in a heart having a septum, left and right atriums, left and right ventricles, and descending and ascending aortas associated with the heart, may include the following components: a pump; a first catheter, having first and second ends, the first end adapted for insertion into the left atrium of the heart, the second end of the first catheter being associated with the pump; a second catheter having first and second ends, the first end adapted to be inserted into a portion of the descending aorta, the second end of the second catheter being associated with the pump; and a third catheter having first and second ends, the first end adapted for insertion into the ascending aorta, the third catheter having an aortic valve prosthesis associated with the second end of the third catheter, whereby upon disposing the aortic valve prosthesis within the diseased aortic valve and implanting the aortic valve prosthesis within the diseased aortic valve, oxygenated blood from the left atrium may be pumped into the descending aorta, during a period of time while the aortic valve prosthesis is being implanted within the diseased aortic valve.

In accordance with this aspect of the present invention, a feature of the apparatus may be that the pump is an external pump. The aortic valve prosthesis may include a stent, and the stent may be mounted on the first end of the third catheter. The stent may be a self-expanding stent, or the stent may be a balloon-expandable stent. If a balloon-expandable stent is utilized, the third catheter may be a dilatation catheter. Another aspect of the apparatus is that the pump may be an external centrifugal pump. Another feature of the apparatus is that the first end of the first catheter may be adapted to pierce the septum between the right and left atriums to enter the left atrium.

The method and apparatus for implanting an aortic valve of the present invention, when compared to previously proposed methods and apparatus, is believed to have the advantages of: not requiring surgery, or incisions, upon the heart itself, may be readily performed percutaneously without chest surgery and without complete loss of blood flow from the heart to the patient's body; and may be transluminally implanted in a cardiac catheterization lab setting with minimal blood loss and relatively low risk of morbidity and mortality.

While the invention will be described in connection with the preferred embodiments shown herein, it will be understood that it is not intended to limit the invention to those embodiments. On the contrary, it is intended to cover all alternatives, modifications, and equivalents, as may be included within the spirit and the scope of the invention as defined by the appended claims.

DETAILED DESCRIPTION OF THE PREFERRED EMBODIMENTS

Before describing the method and apparatus of the present invention, a brief description of the functioning of heart 73 (FIG. 2) and associated arteries is provided. In general, the heart 73 consists of two pumps lying side by side. Each pump has an upper chamber, or atrium, and a lower chamber, or ventricle, as will hereinafter be described. Heart 73 functions to provide a person's body 79 (FIG. 1) with a continuous supply of blood as illustrated by arrows 81. In general, the right side of heart 73 receives "used" blood from the veins (not shown) of a person's body, and this blood is pumped to the lungs (not shown) of the person's body to be oxygenated. The oxygen-rich blood from the lungs is then returned to the left side of the heart, which pumps it through the various arteries. Heart 73 requires its own supply of blood to keep it beating. Oxygen-rich blood is pumped to the chambers, or ventricles, of the heart through the coronary arteries, as will be hereinafter described. Once the blood has been used, it is returned to the right side of heart 73 through a network of veins.

Figure 2:
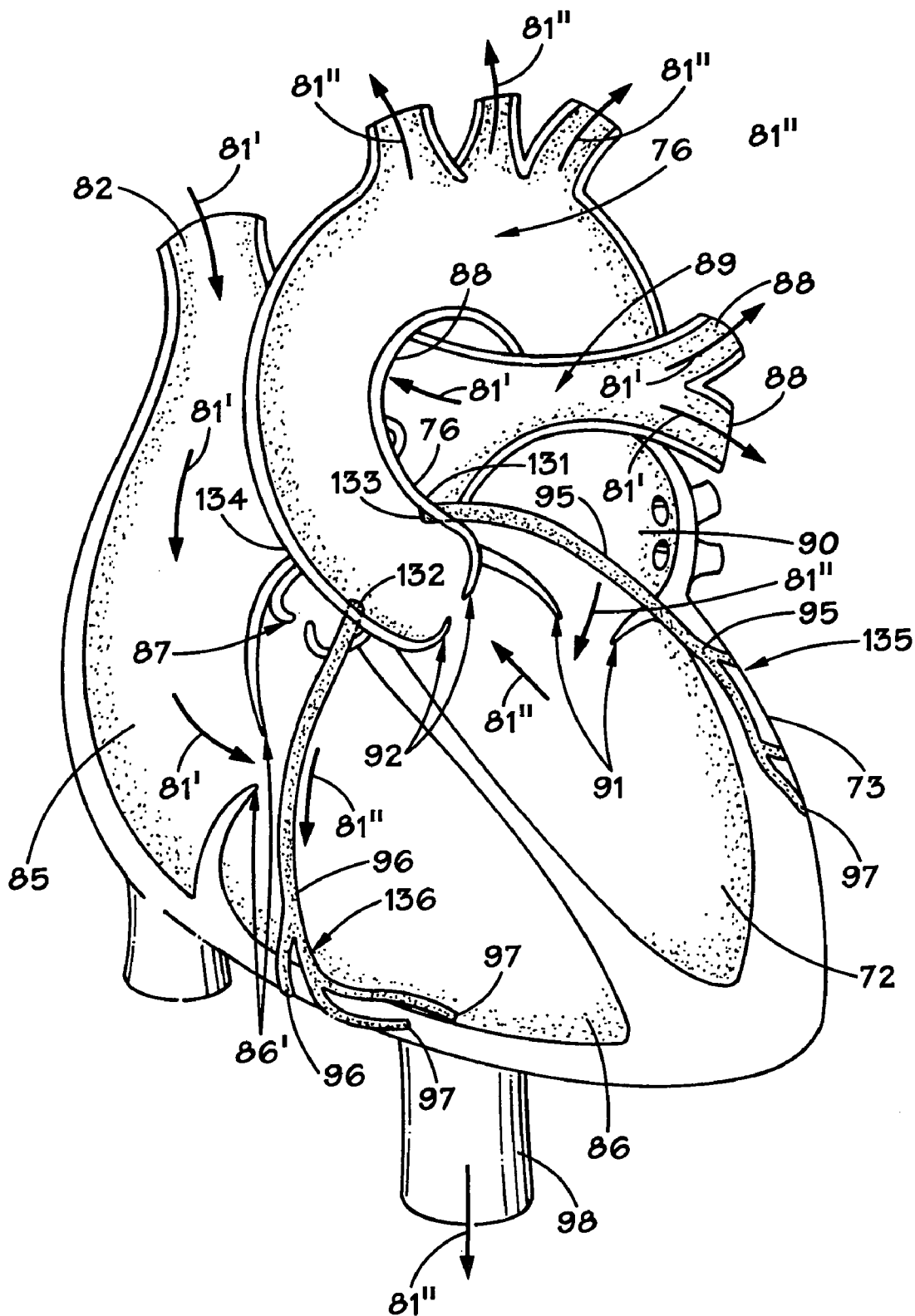
FIG. 2 is an enlarged, partial cross-sectional view of a heart, to illustrate its functions and anatomy.

The functioning of these elements of heart 73 may be described in connection with FIG. 2. Deoxygenated blood flows from veins, such as vein 82 into the right atrium, or right upper chamber, 85 of heart 73, as illustrated by arrows 81'. Deoxygenated blood 81' then flows through the one-way tricuspid valve, or right atrioventricular valve, 86' into the right lower chamber, or right ventricle, 86 of heart 73. Contraction of the muscle surrounding right ventricle 86 pumps the blood through the semilunar valve, or pulmonary valve 87, and along the pulmonary arteries 88 through the lungs (not shown), where the deoxygenated blood 81' receives oxygen. The ascending pulmonary artery is designated 89, from which pulmonary arteries 88 branch. Oxygenated blood, as represented by arrows 81" flows from the lungs into the left upper chamber, or left atrium, 90 and then passes downwardly through mitral valve, or left atrioventricular valve, 91 into the left lower chamber, or left ventricle, 72. Muscle surrounding the left ventricle 72 contracts and pumps the blood 81" through the semilunar valve, or aortic valve, 92 (which may be diseased) into the aorta, or ascending aorta, 76, and descending aorta 98. The oxygenated blood 81" is then circulated through the body's arteries and ultimately returned as deoxygenated blood 81' to the right side of heart 73 as previously described. As previously described, oxygen-rich blood 81" is pumped to the left and right sides of heart 73 through the left coronary artery 95 and right coronary artery 96. As previously described, once the oxygen-rich blood 81" has been used, the blood is returned to the right side of the heart through a network of veins 97.

Figure 1:
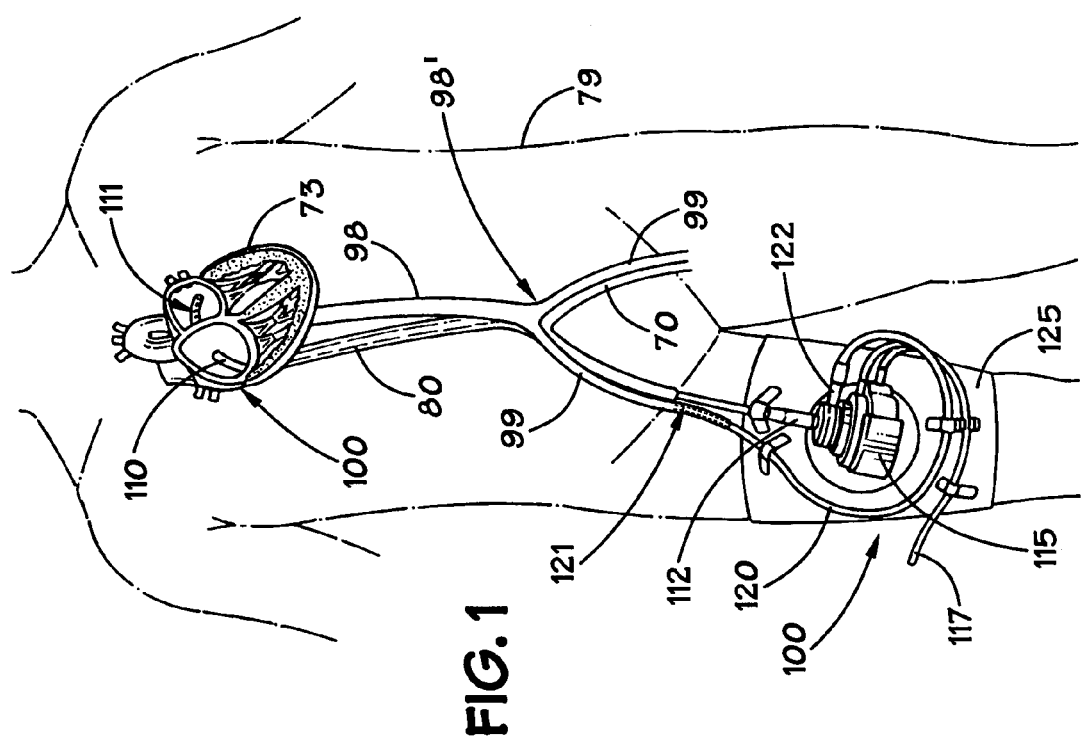
FIG. 1 is a front view of a person's body provided with parts of the apparatus of the present invention.

With reference to FIG. 1, heart 73 is disposed within the patient's, or person's, body 79 and parts, or components, of the apparatus 100 for repairing a diseased aortic valve, such as valve 92 (FIG. 2) as illustrated. FIG. 1 illustrates the person's: descending aorta 98; iliac arteries 99 which join the aorta 98 at the aortic bifurcation 98; and femoral artery, or vein, 70 which leads into the inferior vena cava 80.

Figure 3:
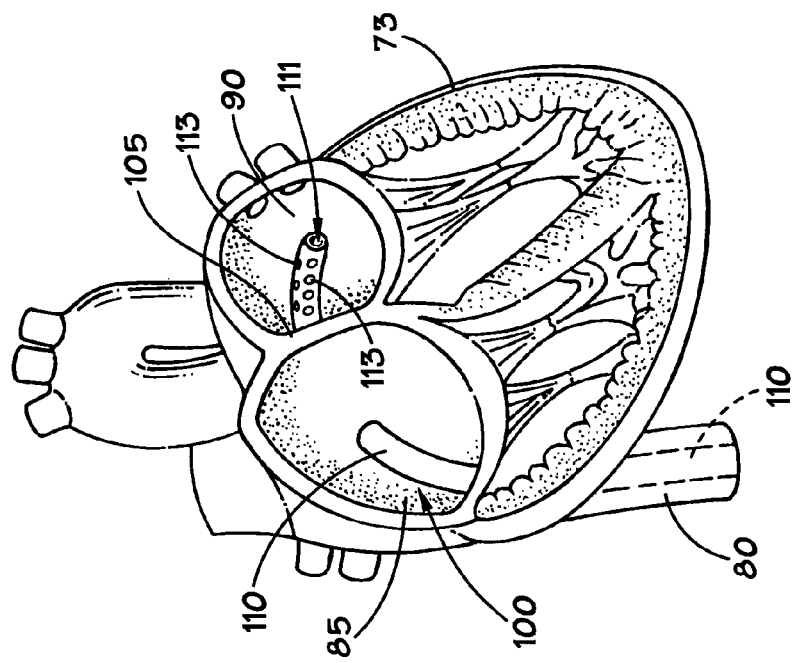
FIG. 3 is a partial cross-sectional view of the heart shown in FIG. 1 with a part of the present invention disposed in the heart.

With reference to FIG. 3, heart 73 has been enlarged and a septum, or dividing wall, 105 between the right atrium 85 and the left atrium 90 is shown. As will be hereinafter described in greater detail, a portion of apparatus 100, or a first catheter, or cannula, 110, having a first end 111 is inserted, or delivered, into the left atrium 90. Catheter 110 has entered the left atrium 85 via the inferior vena cava 80, and has pierced septum 105, whereby first end 111 of the first catheter 110 is disposed within the left atrium 90. A standard, conventional transseptal technique may be utilized to pass the first end 111 of the first catheter 110 into the left atrium 90.

With reference to FIGS. 1 and 3, the second end 112 of the first catheter 110 is associated with a pump 115 in a fluid, or blood, transmitting relationship. A second catheter 120 having first and second ends 121, 122, has its first end 121 inserted, or delivered, into a portion of the descending aorta 98, or preferably into one of the iliac arteries 99. Second end 122, of second catheter 120, is also associated with pump 115 in a fluid, or blood, transmitting relationship. The connections between the second end 112 of catheter 110 and second end 122 of catheter 120 provide a fluid transmitting relationship between the catheters 110, 120 and pump 115, as will hereinafter be described in greater detail. Pump 115 is preferably an external pump, in that it is disposed externally of the patient's body 79, and in the embodiment illustrated in FIG. 1 may be disposed upon a strap 125, whereby pump 115 is mounted on the exterior surface of the patient's thigh.

Figure 4:
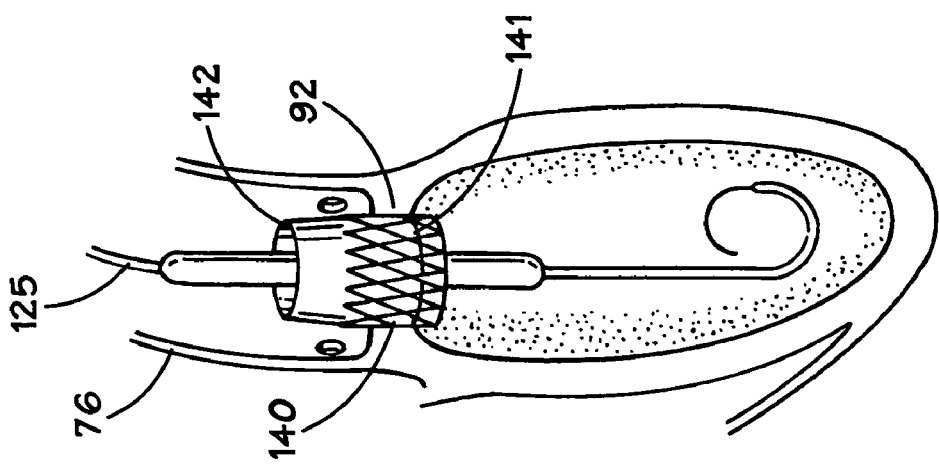
FIGS. 4-6 are partial cross-sectional views of the left ventricle of the heart of FIGS. 1 and 2, illustrating implantation of an aortic valve prosthesis in accordance with the present invention.
Figure 5:
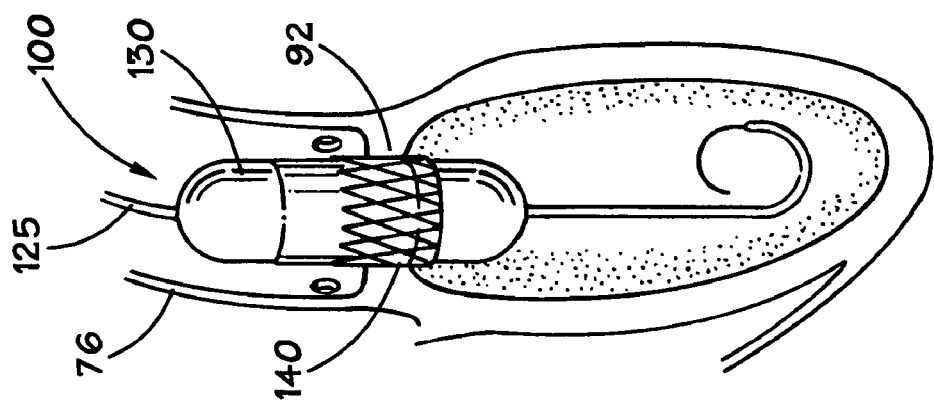
Figure 6:
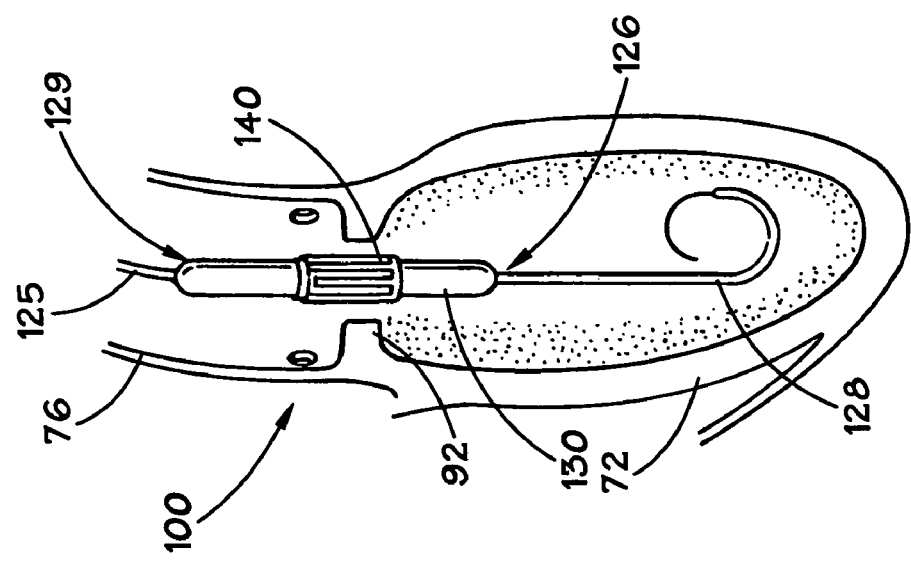

With reference now to FIGS. 4-6, other parts, or components of apparatus 100 are shown in connection with the left ventricle 72 and ascending aorta 76 of a patient with a diseased aortic valve 92. These components of apparatus 100 include a third catheter 125 having first and second ends 126, 127, with an aortic valve prosthesis 140 associated with the first end 126 of third catheter 125. As is conventional, a guide wire 128 may pass through third catheter 125 and may be utilized in the introduction and insertion of third catheter 125 into the ascending aorta 76 and to a location adjacent, or proximate, to the diseased aortic valve 92. The second end 127 (not shown) of third catheter 125 may include conventional connections and fittings to permit the third catheter 125 to function in a manner as will hereinafter be described. Preferably, the third catheter 125 is a dilatation, or balloon, catheter 129; however, other types of catheters, or percutaneous delivery devices, could be utilized to deliver and implant aortic valve prosthesis 140. If a dilatation catheter 129 is utilized as the third catheter 125, it may be inflated and expanded in a conventional manner, as is known in the field of medicine. In FIG. 4, the balloon, or dilatation portion, 130 of third catheter 125 is shown in its uninflated condition, wherein third catheter 125 has a first, reduced diameter permitting its insertion and delivery to the desired site adjacent, or proximate, the diseased aortic valve 92.

With reference to FIG. 5, the balloon 130 of balloon catheter 129 is illustrated in its second expanded, inflated configuration to assist in the implantation of the aortic valve prosthesis 140, as will be hereinafter described in greater detail. In FIG. 6, the balloon 130 of catheter 129 has been deflated, to assume a decreased diameter to permit balloon catheter 129 to be removed from the aortic valve prosthesis 140 and from the ascending aorta 76, as is known in the field of medicine.

With reference to FIGS. 4-6, aortic valve prosthesis 140 may include a frame, or stent, 141 and an aortic valve 142. In FIG. 4, the stent and valve 141, 142 are initially in a first reduced diameter configuration upon third catheter 125, to permit the insertion and delivery of the aortic valve prosthesis 140 to the desired site adjacent the diseased aortic valve 92. In FIGS. 5 and 6, the stent 141 and valve 142 are in a second enlarged configuration, wherein the aortic valve prosthesis has been implanted and secured within the diseased aortic valve 92. In the embodiment illustrated in FIGS. 4-6, wherein a dilatation, or balloon catheter 129 is utilized, the aortic valve prosthesis 140 is caused to assume its second expanded configuration from the inflation and expansion of balloon 130 of the balloon catheter 129. In the embodiment of FIGS. 4-6, stent 141 is preferably a balloon expandable stent as are known in the art. Alternatively, as is known in the art, stent 141 could be a self-expanding stent which may be delivered by third catheter 125. Typically, self-expanding stents are used with catheters which have an outer sheath (not shown) which retains the self-expanding stent in its first reduced diameter configuration, and upon removal of the sheath, or other similar structure, or other stent activation device, the self-expanding stent expands outwardly into engagement with the diseased aortic valve 92. An example of the catheter 125 and aortic valve prosthesis 140 which may be used in the present apparatus 100 is illustrated and described in the previously referred to United States Patent Application Publication No. U.S. 2003/0109924.

Figure 7:
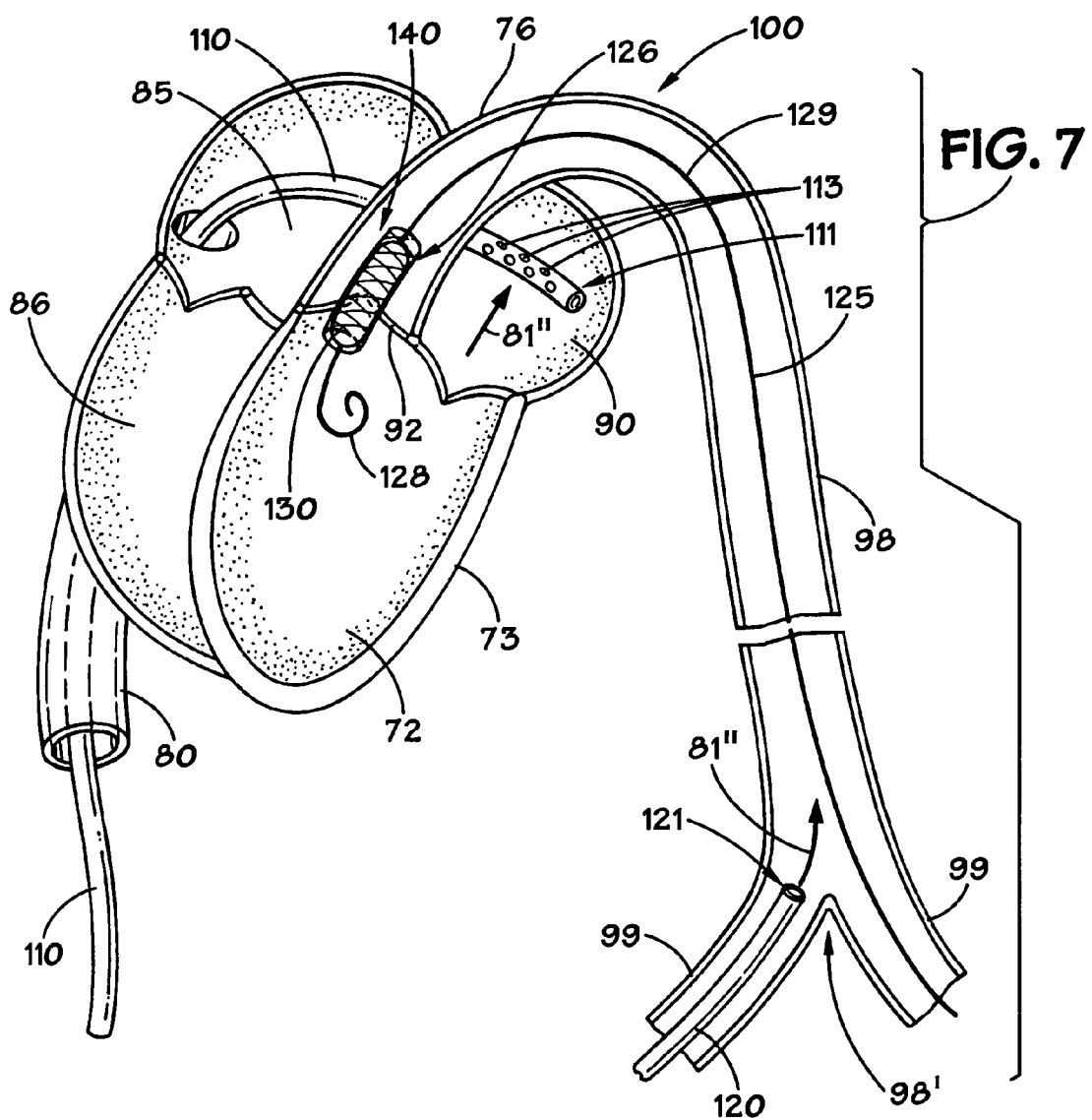
FIG. 7 is partial cross-sectional view of a patient's body illustrating implantation of an aortic valve prosthesis in accordance with the present invention.

With reference to FIGS. 1 and 7, the method for percutaneously implanting an aortic valve prosthesis in accordance with the present invention will be described. The patient, who preferably is in a catheterization laboratory of a hospital (or alternatively dependent upon the circumstances, in a surgical suite) has the first catheter 110 percutaneously inserted into the patient's femoral artery and vein on either the right or left leg of the patient, insertion in the right leg being illustrated in FIG. 1 for illustrative purposes only. First catheter 110 is then passed into the inferior vena cava 80 until it enters the right atrium 85, and at least a portion of the first catheter 110, generally its first end 111, is passed through, or pierces, the septum 105 (FIG. 3) until the first end 111 of catheter 110 enters the left atrium 90. The catheter, or cannula, 100 is passed through septum 105 by use of any suitable technique, such as a standard transseptal technique. First catheter 110 may be preferably provided with a plurality of openings 113 through which oxygenated blood 81" from the left atrium may enter first catheter 110. As previously described, the second end 112 of first catheter 110 is associated in a fluid transmitting relationship with pump 115.

Second catheter, or venous cannula, 120 may then be percutaneously delivered into a portion of the descending aorta 98, preferably, into one of the iliac arteries 99, whereby the first end 121 of the second catheter 120 is disposed within the descending aorta 98, preferably adjacent, or proximate, the aortic bifurcation 98'. The second end 122 of catheter 120, as previously described, is also associated with pump 115 in a fluid transmitting relationship. By operation of pump 115, oxygenated blood 81" may be drawn outwardly from left atrium 90 through first catheter 110, and via pump 115 the oxygenated blood 81" is pumped outwardly into the descending aorta 98. Preferably the two catheters 110, 120 and pump 115 will be de-aired before operation of pump 115. Thereafter, pump 115 will be operated to pump oxygenated blood 81"0 into the descending aorta 98. Pump 115 may be provided with power in any suitable manner, such as by use of an external battery or other power source (not shown) via power cord 117 (FIG. 1). Pump 115 will be operated at a relatively low pump speed until such time as a physician is ready to implant the aortic valve prosthesis 140, at which time the patient will be fully anticoagulated in a conventional manner. Alternatively, the second catheter 120 could be first inserted and the first catheter 110 could thereafter be inserted.

With reference to FIGS. 1 and 4-7, the third catheter 125, with aortic valve prosthesis 140 associated therewith, is then percutaneously delivered into the ascending aorta 76. As previously described, the third catheter 125 has the aortic valve prosthesis 140 associated with the third catheter 125, preferably at or proximate, the first end 126 of third catheter 125. The third catheter 125 may initially be percutaneously inserted into the femoral artery and vein of the other leg—in the embodiment illustrated, the patient's left leg. Catheter 125 then passes into and through the iliac artery 99 upwardly through descending aorta 98 and then into the descending aorta 76. The first end 126 of the third catheter 125 and the aortic valve prosthesis 140 may then be disposed above and adjacent the diseased aortic valve 92.

Still with reference to FIGS. 1 and 4-7, the pump speed of pump 115 is then preferably increased to provide a safe, maximum flow of oxygenated blood 81" into the descending aorta 98. Thereafter, the third catheter 125 maybe be further moved, whereby the aortic valve prosthesis 140 is disposed within the diseased aortic valve 92, as shown in FIG. 4. Thereafter, in the embodiment of third catheter 125 being a balloon catheter 129, balloon 130 may be inflated, or dilated, to expand stent 141 to its expanded diameter configuration shown in FIGS. 5 and 7, whereby aortic valve prosthesis 140 is implanted within diseased aortic valve 92. While diseased aortic valve 92 is occluded by the expanded balloon 130, operation of pump 115 at its maximum safe speed will permit complete unloading of the left ventricle 72, and the patient will be supported by the flow of oxygenated blood 81" into the descending aorta 98. During this time, the physician will have adequate time to correctly and precisely locate and implant the aortic valve prosthesis 140 within the diseased aortic valve 92, without fear of complications arising from a lack of oxygenated blood 81" flow within the patient's body.

With reference to FIG. 6, after the aortic valve prosthesis 140 has been properly implanted within the diseased aortic valve 92, balloon 130 may be deflated, and balloon 130 and third catheter 125 may be removed from the patient, at which time the pump speed of pump 115 will be reduced until blood flow has resumed through the implanted aortic valve prosthesis 140. Thereafter, the first and second catheters 110, 120 may also be removed and the femoral arteries sutured at the point of insertion of the catheters.

If stent 141 of aortic valve prosthesis 140 is a self-expanding stent, and a different type of catheter is used as the third catheter 125, the procedure to implant the aortic valve prosthesis 140 would be generally the same as that procedure previously described, with the exception that stent 141 would be permitted to achieve self-expansion into its second expanded diameter as illustrated in FIGS. 5-7 to achieve implantation of aortic valve prosthesis 140.

It is to be understood that the invention is not limited to the exact details of construction, operation, exact materials or embodiments shown and described, as modifications and equivalents will be apparent to one skilled in the art. Accordingly, the invention is therefore to be limited only by the scope of the appended claims.

What is claimed is:

1. A method for percutaneously implanting an aortic valve prosthesis in a beating heart having a septum, left and right atriums, left and right ventricles, a diseased aortic valve, and descending and ascending aortas associated with the beating heart, comprising the steps of:

percutaneously delivering a portion of a first catheter into the left atrium of the beating heart, the first catheter being associated with a pump;

percutaneously delivering a second catheter into a portion of the descending aorta, the second catheter being associated with the pump;

percutaneously delivering a third catheter into the ascending aorta, the third catheter having an aortic valve prosthesis associated with the third catheter;

disposing the aortic valve prosthesis within the diseased aortic valve and implanting the aortic valve prosthesis within the diseased aortic valve; and pumping oxygenated blood from the left atrium into the descending aorta, during a period of time while the aortic valve prosthesis is being implanted within the diseased aortic valve.

2. The method of claim 1, including the steps of: removing the first catheter from the left atrium; removing the second catheter from the descending aorta; and
removing the third catheter from the ascending aorta.

3. The method of claim 1, wherein the period of time while the oxygenated blood is being pumped begins shortly before the aortic valve prosthesis is being implanted and ends after the aortic valve prosthesis has been implanted.

4. The method of claim 1, including the steps of pumping the oxygenated blood through the first catheter into the pump, and then pumping the oxygenated blood through the second catheter.

5. The method of claim 1, including the step of utilizing an external pump as the pump.

6. The method of claim 4, including the step of utilizing an external pump as the pump.

7. The method of claim 1, including the steps of utilizing as the aortic valve prosthesis, an aortic valve prosthesis which includes a stent, and mounting the stent on the third catheter.

8. The method of claim 7, including the step of utilizing a self-expanding stent as the stent.

9. The method of claim 7, including the steps of: utilizing a balloon expandable stent as the stent; utilizing a dilatation catheter as the third catheter; and expanding the stent with the dilatation catheter.

10. The method of claim 1, including the steps of: delivering the first catheter through a femoral vein into the right atrium; and then delivering a portion of the first catheter through the septum of the heart into the left atrium.

* * * * *